United States Patent [19]

Pfiffner et al.

[11] Patent Number: 5,403,388
[45] Date of Patent: Apr. 4, 1995

[54] SURFACTANT MEDIATION SPARGE TUBE

[76] Inventors: Tim E. Pfiffner; Steve M. Shatkin, both of P.O. Box 6089, Santa Rosa, Calif. 95406

[21] Appl. No.: 60,446

[22] Filed: May 12, 1993

[51] Int. Cl.⁶ ............................................. B01D 19/02
[52] U.S. Cl. ...................... 96/176; 95/242; 96/179; 436/178
[58] Field of Search ................. 96/176–180; 95/242; 436/177, 178

[56] References Cited

U.S. PATENT DOCUMENTS

| | | | |
|---|---|---|---|
| 2,262,018 | 11/1941 | Lighton | 95/242 X |
| 3,898,045 | 8/1975 | Bowley | 96/179 X |
| 4,073,622 | 2/1978 | Luppi | 96/179 X |
| 4,963,169 | 10/1990 | Granville | 96/178 |
| 5,015,273 | 5/1991 | Hamilton et al. | 96/179 X |

FOREIGN PATENT DOCUMENTS 1411002 7/1988 U.S.S.R. ................... 96/176

Primary Examiner—Richard L. Chiesa
Attorney, Agent, or Firm—Larry D. Johnson

[57] ABSTRACT

A surfactant mediation sparge tube for use with analytical instruments includes a two part purge vessel having an upper portion attached to a lower portion by a coupling device, an inner foam directing tube carried by a non-permeable disk positioned generally between the purge vessel upper and lower portions, and an internal physical foam barrier positioned in the purge vessel upper portion. The foam directing tube and disk, which may be fixed or removable, seals the lower portion of the vessel from the upper portion, directing purge gas and foam to the upper portion of the vessel only via the inner foam directing tube.

8 Claims, 3 Drawing Sheets

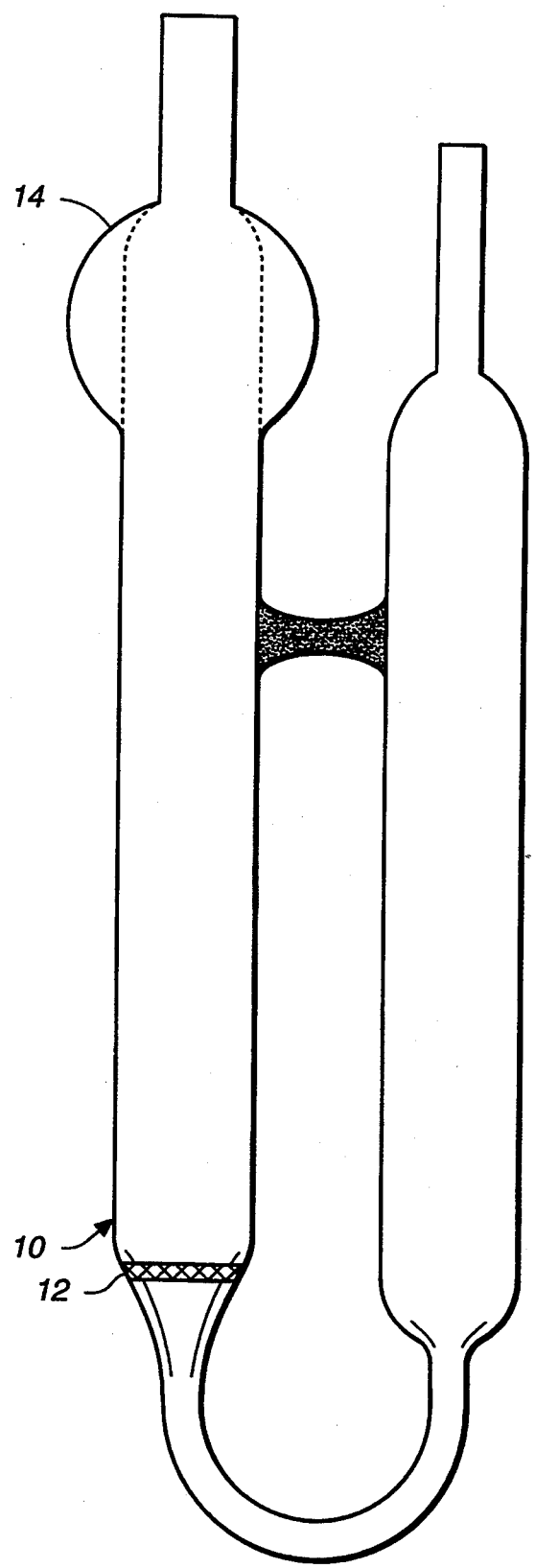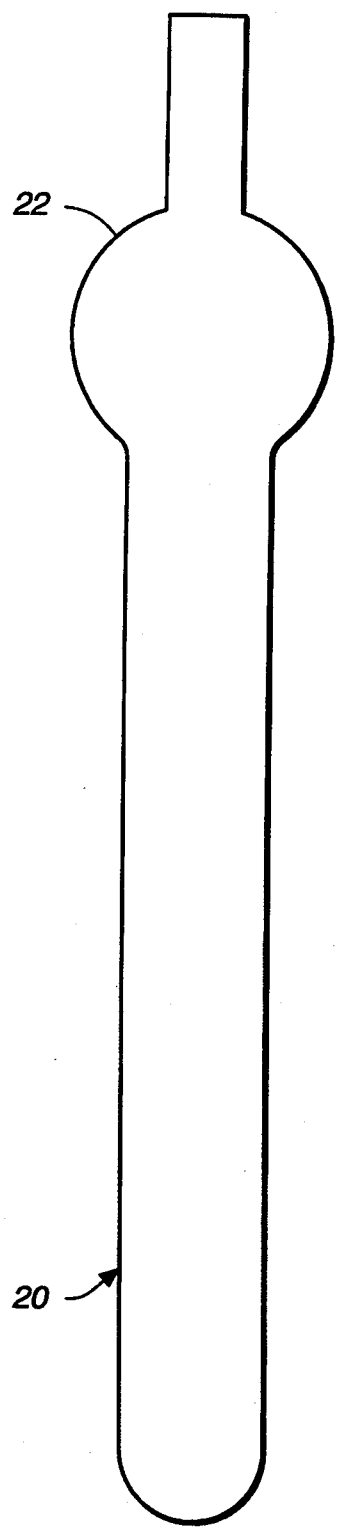
FIG._1A
(PRIOR ART)
FIG._1B
(PRIOR ART)

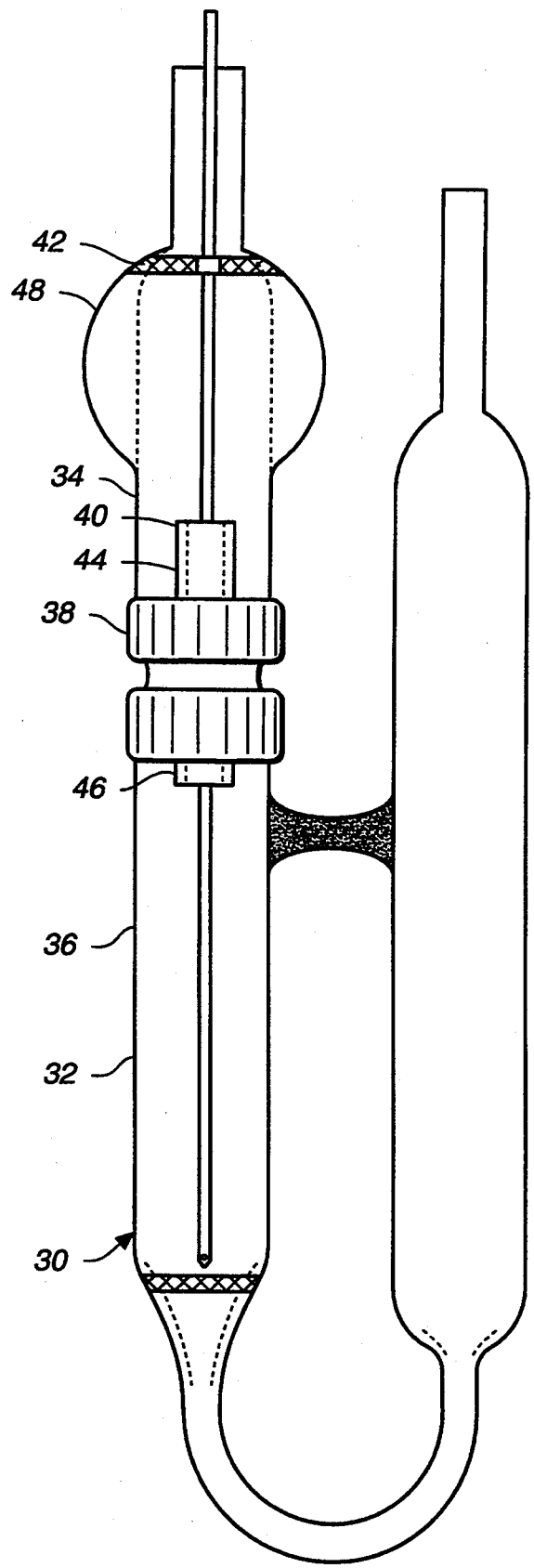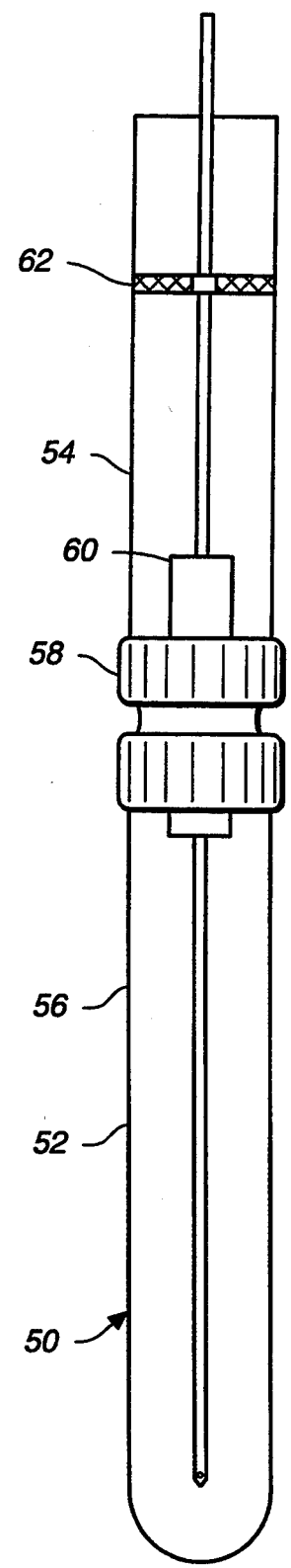
FIG._2   FIG._3

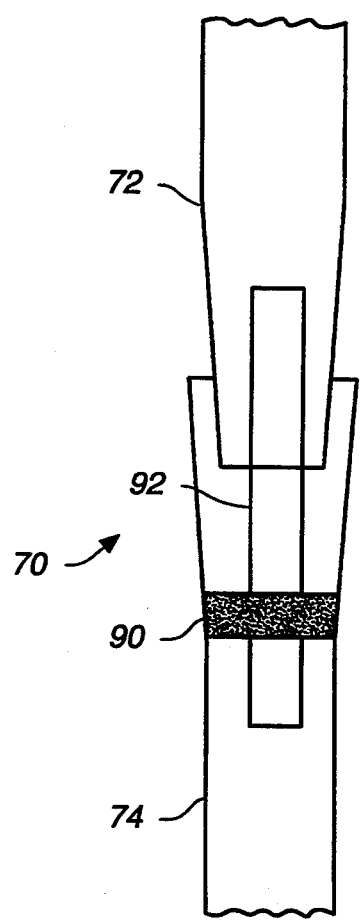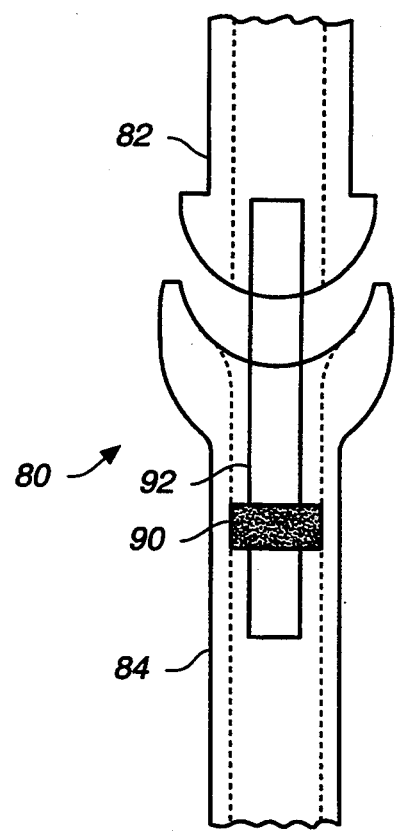
FIG._4  FIG._5

SURFACTANT MEDIATION SPARGE TUBE

BACKGROUND OF THE INVENTION

1. Field of the Invention

This invention relates generally to environmental testing apparatus and associated hardware, and more specifically to an improved foam protecting purge vessel for use with analytical instruments.

2. Description of the Prior Art

One of the inherent difficulties with conducting purge and trap analysis on various environmental matrices is the problem of surfactant-laden or "foamy" samples. Foamy samples present several problems when methods call for purge and trap analysis and standard purge vessels are employed. As the foamy sample purges and the foam level reaches the top of the sparge tube, the foam is often pushed by the gas stream onto the trap, thus saturating the trap with a liquid rather than the intended gas. This effect can result in major instrument contamination, especially if the surfactant permeates the trap and enters the gas chromatograph and subsequent detectors. More importantly, from an analytical standpoint, low level or normal operating detection levels may be seldom attainable due to the number of dilutions needed to prevent the sample from foaming in the sparge vessel. If automated instrumentation is employed, subsequent samples may be highly susceptible to analytical error due to cross-contamination from the initial foamy sample. Costly and time consuming re-analysis of the sample set and decontamination of the instrumentation may then be necessary to insure the integrity of the ensuing analytical data.

SUMMARY OF THE INVENTION

The surfactant mediation sparge tube of this invention provides a novel foam protecting purge vessel for use with analytical instruments. The inventive design comprises a two part purge vessel having an upper portion and a lower portion, an inner "foam directing tube" carried by a non-permeable disk positioned generally between the purge vessel upper and lower portions, and an internal physical foam barrier positioned in the purge vessel upper portion. The purge vessel upper portion is attached to the lower portion by means of one of several coupling devices including, but not limited to, tapered joints, ball joints, or threaded couplers. The inner foam directing tube and non-permeable disk are situated within the internal diameter of the purge vessel or the coupling device. The inner foam directing tube and disk, which may be fixed or removable, seals the lower portion of the purge vessel from the upper portion, directing purge gas and foam to the upper portion of the vessel only via the inner foam directing tube.

The inner foam directing tube and disk are the primary means of mediating the surfactant within the purge vessel. Extending several centimeters into the upper portion of the purge vessel, the inner tube "directs" any foam passing through it, out the top and down the sides of the tube. The surfactant slides down the sides of the inner tube where it is reservoired above the non-permeable disk, thus preventing the foam from being re-purged and re-foaming, allowing only purge gas to continue through the purge vessel and into the trap. Optionally, the inner foam directing tube also extends some distance downwards into the lower portion of the purge vessel, creating a dead space above its entry and the non-permeable disk above, which dead space acts to capture and break down a portion of the foam.

The upper portion of the purge vessel is the secondary means of surfactant mediation. The design may be either a straight cylinder, or a cylinder which expands into a greater internal volume such as a sphere. In either design, a fixed or removable porous frit member is incorporated into the purge vessel at the uppermost section, before the purge vessel is attached to the purge and trap device. This frit member acts as an internal physical barrier if the volume of foam purged exceeds the capacity of the lower vessel, upper vessel reservoir, and total upper vessel volume. The design has been shown not to effect internal standard, surrogate standard, or laboratory fortified blanks.

The inventive apparatus has been shown to successfully overcome the problems described above by significantly reducing the possibility of foam from passing through the purge vessel and into the trap or analytical instrument. As a consequence of this foam protection, the need for subsequent sample dilution is reduced, thereby lowering detection limits and preserving sample integrity, specifically when analyzing for volatile organic compounds. Additionally, instrument and detector contamination is significantly minimized, thereby reducing instrument downtime and sample re-runs.

BRIEF DESCRIPTION OF THE DRAWINGS

FIG. 1A is a side elevation view of a prior art typical purge vessel, illustrating a basal frit element and an optional upper foam trap portion;

FIG. 1B is a side elevation view of a prior art typical needle sparger, also illustrating an optional upper foam trap portion;

FIG. 2 is a side elevation view of a surfactant mediation sparge tube of this invention illustrating a two part purge vessel having an upper portion and a lower portion joined by a coupling device, an inner foam directing tube and disk positioned generally between the purge vessel upper and lower portions, and an internal physical foam barrier positioned in the purge vessel upper portion;

FIG. 3 is a side elevation view of a surfactant mediation sparge tube needle sparger of this invention, again illustrating a two part purge vessel having an upper portion and a lower portion joined by a coupling device, an inner foam directing tube and disk positioned generally between the purge vessel upper and lower portions, and an internal physical foam barrier positioned in the purge vessel upper portion;

FIG. 4 is a side elevation view of an optional ground taper joint coupling device for the upper and lower portions of the inventive purge vessel; and FIG. 5 is a side elevation view of an optional ball joint coupling device for the upper and lower portions of the inventive purge vessel.

DETAILED DESCRIPTION OF A PREFERRED EMBODIMENT

FIG. 1A is a side elevation view of a prior art typical purge vessel 10, illustrating a basal frit element 12 and an optional upper foam trap portion 14. FIG. 1B is a side elevation view of a prior art typical needle sparger 20, also illustrating an optional upper foam trap portion 22.

FIG. 2 is a side elevation view of a surfactant mediation sparge tube 30 of this invention illustrating a two part purge vessel 32 having an upper portion 34 and a lower portion 36 joined by a threaded coupling device 38, an inner foam directing tube 40 and non-permeable disk (not visible in this view) positioned generally between the purge vessel upper and lower portions, and an internal physical foam barrier 42 positioned in the purge vessel upper portion 34. Inner foam directing tube 40 includes an upper segment 44 and a lower segment 46, each serving to mediate any generated surfactant, as described supra. Purge vessel upper portion 34 may include an optional expanded volume portion 48, as illustrated. Physical foam barrier 42 may comprise a permanent or removable frit element composed of glass, polypropylene, Teflon, or any other suitable material.

The two-part vessel in FIG. 2 can be made from one piece, without the joint. The joint is not critical for the anti-foaming design to work.

FIG. 3 is a side elevation view of a surfactant mediation sparge tube needle sparger 50 of this invention, again illustrating a two part purge vessel 52 having an upper portion 54 and a lower portion 56 joined by a threaded coupling device 58, an inner foam directing tube 60 and non-permeable disk (not visible in this view) positioned generally between the purge vessel upper and lower portions, and an internal physical foam barrier 62 positioned in the purge vessel upper portion 54. Purge vessel upper portion 54 may comprise a straight cylinder, interchangeable with other forms or shapes of purge vessel upper portions such as illustrated in FIG. 2, supra.

Also, in FIG. 3, the vessel could be made from one piece of glass. In fact, one very popular method for purging samples is using inexpensive test tubes. In such an application, a piece consisting of a non-permeable disk and an inner directing foam tube could be slid down inside the test tube to mediate foamy samples.

FIG. 4 is a side elevation view of an optional ground taper joint coupling device 70 for the upper portion 72 and lower portion 74 of the inventive purge vessel, and FIG. 5 is a side elevation view of an optional ball joint coupling device 80 for the upper portion 82 and lower portion 84 of the inventive purge vessel. Each of these views illustrate the non-permeable disk 90 positioned in the purge vessel lower portion, and used to carry the inner foam directing tube 92.

While this invention has been described in connection with preferred embodiments thereof, it is obvious that modifications and changes therein may be made by those skilled in the art to which it pertains without departing from the spirit and scope of the invention. Accordingly, the scope of this invention is to be limited only by the appended claims.

What is claimed as invention is:

1. A surfactant mediation sparge tube for use with analytical instruments, said sparge tube comprising:
   a two part purge vessel having an upper portion and a lower portion;
   an inner foam directing tube carried by a non-permeable disk positioned substantially between said purge vessel upper and lower portions, said inner foam directing tube extending a first distance into said purge vessel upper portion; and
   an internal physical foam barrier positioned in said purge vessel upper portion.

2. The surfactant mediation sparge tube of claim 1 wherein said purge vessel upper portion is attached to said lower portion by means of a coupling device.

3. The surfactant mediation sparge tube of claim 2 wherein said coupling device comprises a threaded coupler.

4. The surfactant mediation sparge tube of claim 2 wherein said inner foam directing tube and said non-permeable disk are situated within the internal diameter of said coupling device.

5. The surfactant mediation sparge tube of claim 1 wherein said inner foam directing tube and said non-permeable disk are removable.

6. The surfactant mediation sparge tube of claim 1 wherein said inner foam directing tube extends a second distance into said purge vessel lower portion.

7. The surfactant mediation sparge tube of claim 1 wherein said purge vessel upper portion comprises a cylinder which expands to create a greater internal volume.

8. The surfactant mediation sparge tube of claim 1 wherein said purge vessel upper portion comprises a porous frit member as an internal physical surfactant barrier.

* * * * *